United States Patent
Wang et al.

(10) Patent No.: US 9,740,818 B1
(45) Date of Patent: Aug. 22, 2017

(54) MODEL IDENTIFICATION AND ANALYSIS OF BIVALENT ANALYTES USING SURFACE PLASMON RESONANCE

(71) Applicants: Xuewen Wang, Miami, FL (US); Yesim Darici, Miami, FL (US); Purushottam Tiwari, Washington, DC (US)

(72) Inventors: Xuewen Wang, Miami, FL (US); Yesim Darici, Miami, FL (US); Purushottam Tiwari, Washington, DC (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/192,234

(22) Filed: Jun. 24, 2016

(51) Int. Cl.
| | | |
|---|---|---|
| G01N 33/48 | (2006.01) | |
| G01N 33/50 | (2006.01) | |
| G06F 19/18 | (2011.01) | |
| G01N 33/543 | (2006.01) | |
| G01N 21/552 | (2014.01) | |
| G06F 19/24 | (2011.01) | |
| G06F 17/11 | (2006.01) | |
| G06F 17/10 | (2006.01) | |

(52) U.S. Cl.
CPC ........... *G06F 19/18* (2013.01); *G01N 21/553* (2013.01); *G01N 33/54373* (2013.01); *G06F 19/24* (2013.01); *G01N 2201/12* (2013.01); *G06F 17/10* (2013.01); *G06F 17/11* (2013.01)

(58) Field of Classification Search
None
See application file for complete search history.

(56) References Cited

PUBLICATIONS

Filion-Cote et al. Design and analysis of a spectro-angular surface plasmon resonance biosensor operating in the visible spectrum. Review of Scientific Instruments, vol. 85, 2014, article 093107, pp. 1-7.*
Tiwari et al. A surface plasmon resonance study of the intermolecular interaction between *Escherichia coli* topoisomerase I and pBAD/Thio supercoiled plasmid DNA. Biochemical and Biophysical Research Communications, vol. 445, 2014, pp. 445-450.*
Toth et al. Study of the subunit interactions in myosin phosphatase by surface plasmon resonance. European Journal of Biochemistry, vol. 267, 2000, pp. 1687-1697.*
Tiwari et al. Analyzing surface plasmon resonance data: Choosing a correct biphasic model for interpretation. Review of Scientific Instruments, vol. 86, Mar. 6, 2015, article 035001, pp. 1-8.*
Tiwari et al. Note: Model identification and analysis of bivalent analyte surface plasmon resonance data. Review of Scientific Instruments, vol. 86, Oct. 19, 2015, article 106107, pp. 1-3.*
Phizicky et al., "Protein-protein interactions: methods for detection and analysis," Microbiological Reviews, Mar. 1995, pp. 94-123, vol. 59, No. 1.

Berggard et al., "Methods for the detection and analysis of protein-protein interactions," Proteomics, 2007, pp. 2833-2842, vol. 7.
Wang et al., "Label-free measuring and mapping of binding kinetics of membrane proteins in single living cells," Nature Chemistry, Oct. 2012, pp. 846-853, vol. 4.
Zhang et al., "High-performance differential surface plasmon resonance sensor using quadrant cell photodetector," Review of Scientific Instruments, Jan. 2003, pp. 150-153, vol. 74, No. 1.
Tao et al., "High resolution surface plasmon resonance spectroscopy," Review of Scientific Instruments, Dec. 1999, pp. 4656-4660, vol. 70, No. 12.
James et al., "TonB induces conformational changes in surface-exposed loops of FhuA, outer membrane receptor of *Escherichia coli*," Protein Science, 2008, pp. 1679-1688, vol. 17, Cold Spring Harbor Laboratory Press.
Solbak et al., "The host-pathogen interaction of human cyclophilin A and HIV-1 Vpr requires specific N-terminal and novel C-terminal domains," BMC Structural Biology, 2011, pp. 1-16, vol. 11, No. 49.
Nakajima et al., "Kinetic analysis of binding between shiga toxin and receptor glycolipid Gb3Cer by surface plasmon resonance," The Journal of Biological Chemistry, Nov. 16, 2001, pp. 42915-42922, vol. 276, No. 46.
Pabbisetty et al., "Kinetic analysis of the binding of monomeric and dimeric ephnns to Eph receptors: correlation to function in a growth cone collapse assay," Protein Science, 2007, pp. 355-361, vol. 16, Cold Spring Harbor Laboratory Press.
Gutierrez-Aguirre et al., "Surface plasmon resonance for monitoring the interaction of potato virus y with monoclonal antibodies," Analytical Biochemistry, 2014, pp. 74-81, vol. 447.
Smith et al., "Interactions between factor XIII and the αC region of fibrinogen," Blood, Mar. 24, 2011, pp. 3460-3468, vol. 117, No. 12.
Suzuki et. al., "Importance of neonatal FcR in regulating the serum half-life of therapeutic proteins containing the Fc domain of human IgG1: a comparative study of the affinity of monoclonal antibodies and Fc-fusion proteins to human neonatal FcR," The Journal of Immunology, Jan. 18, 2010, pp. 1968-1976, vol. 184.
Prince et al., "Functional evaluation of novel soluble insulin-like growth factor (IGF)-II-specific ligand traps based on modified domain 11 of the human IGF2 receptor," Molecular Cancer Therapeutics, Feb. 2007, pp. 607-617, vol. 6, No. 2.
Haupt et al., "The *Staphylococcus aureus* protein Sbi acts as a complement inhibitor and forms a tripartite complex with host complement factor H and C3b," PLoS Pathogens, Dec. 2008, pp. 1-14, vol. 4, No. 12.

(Continued)

*Primary Examiner* — Russell S Negin
(74) *Attorney, Agent, or Firm* — Saliwanchik, Lloyd & Eisenschenk

(57) ABSTRACT

Methods, software, systems, and apparatuses that can identify bivalent reaction mechanisms using surface plasmon resonance (SPR) are provided. Methods, software, systems, and apparatuses that can identify SPR sensorgrams that fit a bivalent analyte model are also provided. A method can include recording multiple SPR sensorgrams with an analyte at different concentrations, fitting each sensorgram with a single exponential function with exponents, determining the exponents for each sensorgram and $R^2$ values for each sensorgram, and plotting $R^2$ versus analyte concentration and determining if an optimal concentration exists.

13 Claims, 2 Drawing Sheets

(56) References Cited

PUBLICATIONS

Wilson, "Analyzing biomolecular interactions," Science, Mar. 15, 2002, pp. 2103-2105, vol. 295.

Sikarwar et al., "Surface plasmon resonance characterization of monoclonal and polyclonal antibodies of malaria for biosensor applications," Biosensors and Bioelectronics, 2014, pp. 201-209, vol. 60.

Mulchan et al., "Application of a high-resolution SPR technique for monitoring real-time metal/dielectric interactions," Sensors and Actuators B: Chemical, Jan. 2003, pp. 132-137, vol. 88.

Critchley et al., "Binding of prion proteins to lipid membranes," Biochemical and Biophysical Research Communications, 2004, pp. 559-567, vol. 313.

Hahnefeld et al., "Determination of kinetic data using surface plasmon resonance biosensors," Molecular Diagnosis of Infectious Diseases, 2004, pp. 299-320, Humana Press, Totowa, New Jersey.

Lund-Katz et al., "Surface plasmon resonance analysis of the mechanism of binding of apoA-I to high density ipoprotein particles," Journal of Lipid Research, 2010, pp. 606-617, vol. 51.

Riesner et al., "Distinct steps in the specific binding of tRNA to aminoacyl-tRNA synthetase: temperature-jump studies on the serine-specific system from yeast and the tyrosine-specific system from *Escherichia coli*," European Journal of Biochemistry, Jun. 8, 1976, pp. 71-80, vol. 68.

Bernet et al., "Kinetic analysis of the interactions between vaccinia virus complement control protein and human complement proteins C3b and C4b," Journal of Virology, Sep. 2004, pp. 9446-9457, vol. 78, No. 17.

Rich et al., "Survey of the year 2005 commercial optical biosensor literature," Journal of Molecular Recognition, Aug. 2006, pp. 478-534, vol. 19.

Gesellchen et al., "Direct optical detection of protein-ligand interactions," Methods in Molecular Biology: Protein-Ligand Interactions, 2005, pp. 17-46, Humana Press, Totowa, New Jersey.

Ghiotto et al., "PD-L1 and PD-L2 differ in their molecular mechanisms of interaction with PD-1," International Immunology, Jun. 29, 2010, pp. 1-10.

Datta-Mannan et al., "FcRn affinity-pharmacokinetic relationship of five human IgG4 antibodies engineered for improved in vitro FcRn binding properties in cynomolgus monkeys," Drug Metabolism and Disposition, 2012, pp. 1545-1555, vol. 40, No. 8.

Mol et al., "Changes in structural dynamics of the Grb2 adaptor protein upon binding of phosphotyrosine ligand to its SH2 domain," Biochimica et Biophysica Acta 1700, 2004, pp. 53-64.

Futamura et al., "Two-step mechanism of binding of apolipoprotein E to heparin: implications for the kinetics of apolipoprotein E-heparan sulfate proteoglycan complex formation on cell surfaces," The Journal of Biological Chemistry, Feb. 18, 2005, pp. 5414-5422, vol. 280, No. 7.

Alam et al., "Qualitative and quantitative differences in T cell receptor binding of agonist and antagonist ligands," Immunity, Feb. 1999, pp. 227-237, vol. 10.

Sprague et al., "pH-dependence and stoichiometry of binding to the Fc region of IgG by the herpes simplex virus Fc receptor gE-gI," Journal of Biological Chemistry, Jan. 20, 2004, pp. 1-38.

Giannetti et al., "Mechanism for multiple ligand recognition by the human transferrin receptor," PLoS Biology, 2003, pp. 341-350, vol. 1, No. 3.

Lo et al., "The structural basis of actinomycin D-binding induces nucleotide flipping out, a sharp bend and a left-handed twist in CGG triplet repeats," Nucleic Acids Research, Feb. 13, 2013, pp. 4284-4294, vol. 41, No. 7.

Azoitei et al., "Computational design of high-affinity epitope scaffolds by backbone grafting of a linear epitope," Journal of Molecular Biology, 2012, pp. 175-192, vol. 415.

"Curve fitting," Origin User's Manual, Sep. 2014, pp. 509-594, http://www.originlab.com/pdfs/16_CurveFitting.pdf.

Morton et al.,"Interpreting complex binding kinetics from optical biosensors: a comparison of analysis by linearization, the integrated rate equation, and numerical integration," Analytical Biochemistry, 1995, pp. 176-185, vol. 227.

Tiwari et al., "Quantitative study of protein-protein interactions by quartz nanopipettes," Nanoscale, Jul. 7, 2014, pp. 10255-10263, vol. 6.

Majka et al., "Analysis of protein-DNA interactions using surface plasmon resonance," Advances in Biochemical Engineering/ Biotechnology, 2007, pp. 13-36, vol. 104.

Tsoi et al., "Surface plasmon resonance study of the molecular recognition between polymerase and DNA containing various mismatches and conformational changes of DNA-protein complexes," Biosensors and Bioelectronics, 2004, pp. 1209-1218, vol. 19.

Myszka et al., "CLAMP: a biosensor kinetic data analysis program," Trends in Biochemical Sciences, Apr. 1998, pp. 149-150, vol. 23.

Murthy et al., "A kinetic analysis of the tumor-associated galactopyranosyl-($1\rightarrow 3$)-2-acetamido-2-deoxy-$\alpha$-D-galactopyranoside antigen-lectin interaction," Journal of Chemical Sciences, Jan. 2008, pp. 195-203, vol. 120, No. 1.

Myszka, "Kinetic analysis of macromolecular interactions using surface plasmon resonance biosensors," Current Opinion in Biotechnology, 1997, pp. 50-57, vol. 8.

Nguyen et al., "Biosensor-surface plasmon resonance: quantitative analysis of small molecule-nucleic acid interactions," Methods, 2007, pp. 150-161, vol. 42.

Schuster et al., "Assembly and function of a quaternary signal transduction complex monitored by surface plasmon resonance," Nature, Sep. 23, 1993, pp. 343-347, vol. 365.

Chiu et al., "Sensitivity and kinetic analysis of graphene oxide-based surface plasmon resonance biosensors," Sensors and Actuators B: Chemical, 2014, pp. 35-42, vol. 197.

Somvanshi et al., "Surface plasmon resonance studies and biochemical evaluation of a potent peptide inhibitor against cyclooxygenase-2 as an anti-inflammatory agent," Biochemical and Biophysical Research Communications, 2007, pp. 37-42, vol. 361.

Martin et al., "Characterization of the 2:1 complex between the Class I MHC-related Fc receptor and its Fc ligand in solution," Biochemistry, Sep. 3, 1999, pp. 12639-12647, vol. 38, No. 39.

Wawrzak et al., "Wnt3a binds to several sFRPs in the nanomolar range," Biochemical and Biophysical Research Communications, 2007, pp. 1119-1123, vol. 357.

O'Shannessy et al., "Interpretation of deviations from pseudo-first-order kinetic behavior in the characterization of ligand binding by biosensor technology," Analytical Biochemistry, 1996, pp. 275-283, vol. 236, No. 0167.

Merwe, "Surface plasmon resonance," Protein-Ligand Interactions: Hydrodynamics and Calorimetry, Mar. 1, 2001, pp. 1-50, Oxford University Press.

* cited by examiner

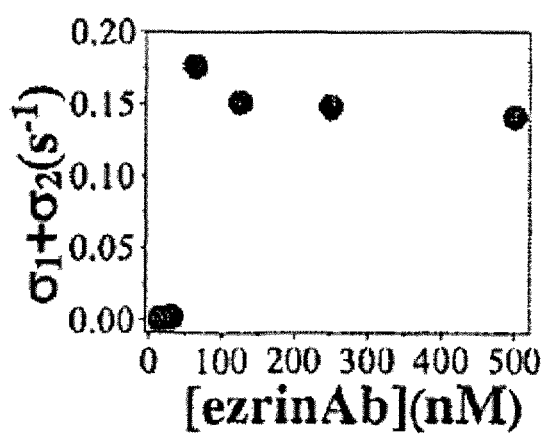
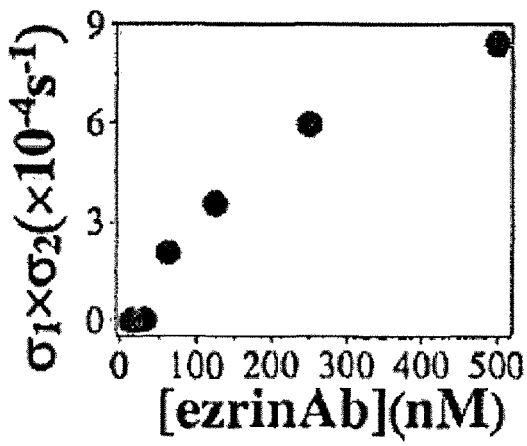
Figure 3a                                  Figure 3b
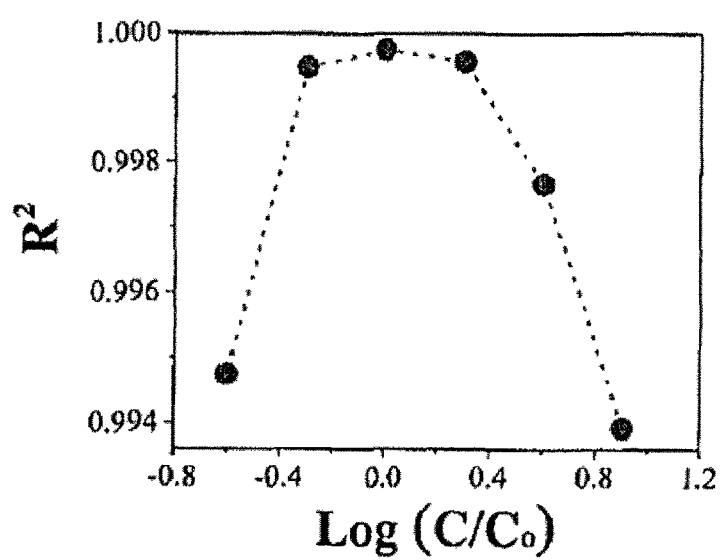
Figure 4

MODEL IDENTIFICATION AND ANALYSIS OF BIVALENT ANALYTES USING SURFACE PLASMON RESONANCE

BACKGROUND OF THE INVENTION

Surface plasmon resonance (SPR) is a widely used, affinity based, label-free biophysical technique to investigate biomolecular interactions. The information gained using SPR can be applied in a multitude of ways. For example, SPR can be used in the medical and pharmaceutical industries in discovering and developing new drugs, studying protein-protein and protein-DNA interactions, and understanding the adsorption of chemical molecules. Surface plasmon resonance can also be used in the food and beverage industry to ensure safety and quality control (e.g., to test for veterinary drug residues in foodstuffs and to test for the presence of genetically modified organisms). However, applications of SPR often require a difficult process of developing models and extracting rate constants.

Obtaining accurate models and rate constants enable a better understanding of the interactions taking place, better predictions and analysis, as well as reduced computing resources. In turn, this leads to SPR being a more effective tool, regardless of the particular industry in which it is applied. Therefore, there is always a need for new and improved ways to analyze SPR data, provide more accurate models, and extract more accurate rate constants.

BRIEF SUMMARY

Embodiments of the present invention include methods, software, systems, and apparatuses that can identify bivalent reaction mechanisms. Embodiments of the present invention also include methods, software, systems, and apparatuses to identify surface plasmon resonance (SPR) sensorgrams that fit a bivalent analyte model.

Embodiments of the present invention can improve SPR analysis, obtain more accurate models and rate constants, reduce computing resources (i.e., make computers more efficient by requiring less processing power and memory) required to analyze and identify the occurrence of bivalent analyte interactions, make computer predictions simpler and more accurate, and provide better predictions of biomolecular interactions. In turn, this leads to SPR being a more effective tool, regardless of the particular industry in which it is applied.

A method for identifying a bivalent reaction mechanism or a bivalent analyte model in SPR sensorgrams can include: recording multiple surface plasmon resonance sensorgrams (i.e., a first batch) with an analyte, with the analyte having a different concentration for each sensorgram; fitting each sensorgram with a single exponential function with exponents; determining the exponents for each sensorgram and $R^2$ values for each sensorgram; and plotting $R^2$ values versus analyte concentration and determining if a maximum exists (i.e., determining if an optimal concentration exists). The method can further include recording a second batch of multiple surface plasmon resonance sensorgrams to perfect the method (to better determine the "optimal concentration", better identify whether a bivalent analyte mechanism is present, and/or better understand the applicability of a bivalent analyte model).

BRIEF DESCRIPTION OF THE DRAWINGS

FIG. 3a is a graph showing the dependency of the sum of the exponents $(\sigma 1+\sigma 2)s^{-1}$ as a function of ezrinAb concentration.

FIG. 3b is a graph showing the dependency of the product of the exponents $(\sigma 1*\sigma 2)s^{-1}$ as a function of ezrinAb concentration.

FIG. 4 is a graph of $R^2$ values versus $\text{Log}(C/C_0)$ obtained by fitting SPR association profiles at different analyte concentrations with a single exponential function.

DETAILED DESCRIPTION

Surface plasmon resonance (SPR) is a well-accepted and label-free tool to investigate and analyze biomolecular interactions, including protein-protein, protein-DNA, and protein-lipid membrane interactions. One category of reaction mechanisms that are studied using SPR is biphasic reaction mechanisms, in which more than one type of interaction is present and contributes to the total response. Neither the simplest equilibrium SPR data analysis method nor the single exponential fitting of SPR profiles can handle biphasic reaction mechanisms. Biphasic reaction models include the two-step conformation change model, the heterogeneous ligand model, the bivalent ligand model, and the bivalent analyte model. However, industry and academia have yet to develop sound methods to identify the bivalent analyte mechanism.

Embodiments of the present invention include methods, software, systems, and apparatuses that can identify bivalent reaction mechanisms. Embodiments of the present invention also include methods, software, systems, and apparatuses to identify SPR sensorgrams that fit a bivalent analyte model.

Embodiments of the present invention can improve SPR analysis, obtain more accurate models and rate constants, reduce computing resources (i.e., make computer more efficient by requiring less processing power and memory) required to analyze and identify the occurrence of bivalent analyte interactions, make computer predictions simpler and more accurate, and provide better predictions of biomolecular interactions. In turn, this leads to SPR being a more effective tool, regardless of the particular industry in which it is applied.

The bivalent analyte model involves coupled non-linear differential equations. This application proposes a unique signature for the bivalent analyte model. This signature can be used to distinguish the bivalent analyte model from other biphasic models. Finally, the proposed method will be demonstrated using in an Example using experimentally measured SPR sensorgrams.

Discussed herein is an approach to identify and analyze the bivalent analyte model that can been used to analyze SPR sensorgrams of a wide range of biomolecular interactions. Measured SPR profiles can often be fitted to different biphasic models with comparable fitting qualities. Therefore, fitting quality alone cannot identify the underlying mechanism. Disclosed herein is an approach that can identify the bivalent model without ambiguity.

Figure 1:
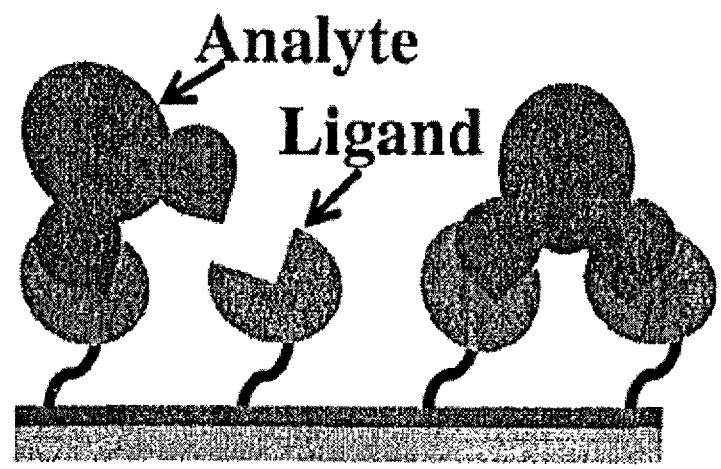
FIG. 1 shows an illustration of a bivalent analyte mechanism.

FIG. 1 is an illustration demonstrating the bivalent analyte mechanism, which is represented by the following two-step process:

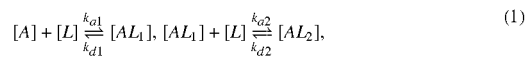

(1)

where [A] represents bivalent analyte, [L] represents ligand, [AL$_1$] represents analyte-ligand complex with one ligand, and [AL$_2$] represents analyte-ligand complex with two ligands bound to single analyte. The $k_a$'s are the association rate constants, and $k_d$'s are the dissociation rate constants. Letting $X_1$ be [AL$_1$] and $X_2$ be [AL$_2$], the density of free ligands on the sensor chip is thus $B_0-X_1-2X_2$, with $B_0$ as the initial ligand concentration. The two-step process of FIG. 1 can then be represented by the following rate equations:

$$\dot{X}_1 = 2k_{a1}C(B_0-X_1-2X_2)-k_{d1}X_1-\dot{X}_2, \quad (2)$$

$$\dot{X}_2 = k_{a2}X_1(B_0-X_1-2X_2)-(2k_{d2})X_2, \quad (3)$$

where C is the concentration of analyte.

Strictly speaking, Equation (3) is only valid when [AL$_1$] is freely mobile in the bulk solution. When [AL$_1$] is restricted within a layer (reaction layer) on a sensor chip, the second association rate constant ($k_{a2}$) needs to be replaced by a two-dimensional (2D) rate constant, $k^*_{a2}$. By comparing Equations (2) and (3), it can be seen that $k_{a1}C$ and $k^*_{a2}X_1$ must have the same unit of s$^{-1}$. It is important to understand that the solution of the rate equations (Equations (2) and (3)) gives 2D density of ligand-analyte complex, not the SPR responses directly. In the following analysis, it will be assumed that SPR responses are proportional to the combined 2D densities $X_1$ and $X_2$.

When rate equations are linear differential equations, it is possible to fit SPR sensorgrams directly with solutions of rate equations. For non-linear rate equation, there is no such simplification. Additionally, non-linear differential equations, in general, have no analytical solutions. Therefore, previously proposed methods cannot be directly applied. Rewriting Equations (2) and (3) in variables $Y=X_1+X_2$ and $X_2$, the rate equations take the form of Equations (4) and (5).

$$\dot{Y} = 2k_{a1}C(B_o-Y)-k_{d1}Y-(2k_{a1}C-k_{d1})X_2, \quad (4)$$

$$\dot{X}_2 = k^*_{a2}(X_2^2-Y^2)+k^*_{a2}B_oY-(k^*_{a2}B_o-2k_{d2})X_2, \quad (5)$$

As expected, Equation (5) is non-linear. However, Equation (4) shows that there exists an "optimal concentration,"

$$C_0 = \frac{k_{d1}}{2k_{a1}},$$

at which the rate equation for Y is independent of $X_2$ and, therefore, is a linear differential equation with an analytical solution of single exponential function, $$Y(t) = \frac{B_0}{2}(1-e^{-(2k_{a1}C_0+k_{d1})t}) = \frac{B_0}{2}(1-e^{-(4k_{a1}C_0)t}). \quad (6)$$

The unknown constant of $B_0$ in Equation (6) does not affect the exponent. The exponent, together with $C_0$, determines $k_{a1}$ and $k_{d1}$. However, at this "optimal concentration" $C_0$, the solution Y(t) does not depend on $k^*_{a2}$ or $k_{d2}$. Therefore, this "optimal concentration" method does not directly obtain these two rate constants. At the optimal concentration, the SPR signal does have contributions from both $X_1(t)$ and $X_2(t)$, but the solution contains no information on the relative strength of these two components.

In practice, the SPR profiles at different analyte concentrations can be fitted individually using a single exponential function, and the fitting errors should have a minimum at the "optimal concentration." The existence of this "optimal concentration" is a unique signature of the bivalent analyte model; it thus can be used to distinguish the bivalent-analyte model from other biphasic models. It is worthwhile to point out that this signature is discarded in any "global" fitting procedure.

A method according to an embodiment of the present invention can include recording multiple surface plasmon resonance sensorgrams (i.e., a first batch) with an analyte, with the analyte having a different concentration for each sensorgram; fitting each sensorgram with a single exponential function with exponents; determining the exponents for each sensorgram and $R^2$ values for each sensorgram; and plotting $R^2$ versus analyte concentration and determining if a maximum exists (i.e., determining if an optimal concentration exists). For the first batch of multiple surface plasmon resonance recordings, it is recommended that at least three recording can be conducted, but it would be beneficial to have five, seven, or even more. This is because, the more recordings you obtain, the more likely you are able to "bracket" the "optimal concentration" within the measurements (i.e., determine the optimal concentration to be within the measured range of concentrations) and predict the "optimal concentration" with greater accuracy. Of course, as discussed below, this can take the form of an iterative process, where an approximate "optimal concentration" is determined and more measurements are taken near where the "optimal concentration" appears to be. The process can consist of two, three, four, five, or more iterations, depending on the desired level of precision Each of the multiple surface plasmon resonance sensorgrams can and generally should be conducted using equivalent chips or sensor surfaces. The single exponential function with exponents can be $$Y(t) = \frac{B_0}{2}(1-e^{-(2k_{a1}C_0+k_{d1})t}) = \frac{B_0}{2}(1-e^{-(4k_{a1}C_0)t}),$$

or an equivalent function. The method can further include determining if the maximum $R^2$ value is over a threshold. The threshold can be, for example, 0.900, 0.910, 0.920, 0.930, 0.940, 0.950, 0.960, 0.970, 0.975, 0.980, 0.985, 0.990, 0.995, 0.998, or 0.999. If the $R^2$ value is over the threshold, it can be concluded that a bivalent analyte reaction mechanism is present and/or a bivalent analyte reaction model is present. The method may further include determining whether the plot of $R^2$ versus analyte concentration takes the form of a quadratic function, which, if it does, suggests that the critical concentration ($C_0$) has been "bracketed" and a bivalent analyte mechanism is occurring or a bivalent analyte model is being demonstrated.

The method can further include fitting each sensorgram with a double exponential function, $$R=D+Ee^{-\sigma_1 t}+Fe^{-\sigma_2 t} \text{ (association)},$$

$$R=Ee^{-\gamma_1 t}+Fe^{-\gamma_2 t} \text{ (dissociation)},$$

or an equivalent exponential function, with D, E, F, $\sigma_1$, $\sigma_2$, $\gamma_1$, and $\gamma_2$ being fitting parameters and wherein D=−(E+F), and plotting $\sigma_1+\sigma_2$ versus analyte concentration and determining if the plot of $\sigma_1+\sigma_2$ versus analyte concentration is non-linear. If it is determined that the plot of $\sigma_1+\sigma_2$ versus analyte concentration is non-linear, then it can be concluded that a bivalent analyte reaction mechanism is present and/or a bivalent analyte reaction model is present. The method can also include plotting $\sigma_1*\sigma_2$ versus analyte concentration and determining if the plot of $\sigma_1*\sigma_2$ versus analyte concentration is either linear or quadratic. If the plot of $\sigma_1*\sigma_2$ versus analyte concentration is either linear or quadratic, it is concluded that a bivalent analyte reaction mechanism is not present and/or a bivalent analyte reaction model is not present.

Methods, software, systems, and apparatuses of embodiments of the present invention can be used in the medical and pharmaceutical fields for drug development and analyzing protein interactions, biomolecular interactions, and DNA interactions. Methods, software, systems, and apparatuses of embodiments of the present invention can be used in the food and beverage industry for product quality control, product development, GMO testing, pesticide testing, and herbicide testing. Methods, software, systems, and apparatuses of embodiments of the present invention can also be used in environmental applications (e.g., for pollutant and remediation analysis). In addition, methods, software, systems, and apparatuses of embodiments of the present invention can be used in veterinary medicine to treat animals, diagnose diseases, or analyze biomolecular interactions. Of course, all of these applications are just examples and are not intended to limit the scope of the present invention.

The methods of the present invention can partially or completely be implemented using a computing device, having one or more processors and memory, to increase measurement prediction accuracy or to increase the efficiency of computing resources. Computing resources are conserved because less computational steps and less memory is required to provide accurate analysis and predictions.

Embodiments of the present invention provide identification and analysis of the bivalent analyte mechanism and model that can be applied to a wide range of SPR experiments. The proposed procedure can first locate an "optimal analyte concentration" by fitting the individual SPR profile at different analyte concentrations to a single exponential function. The method can be of valuable guidance for the SPR users in order to unambiguously identify and analyze the bivalent analyte mechanism and model.

The methods and processes described herein can be embodied as code and/or data. The software code and data described herein can be stored on one or more computer-readable media or machine-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A method for identifying a bivalent reaction mechanism or bivalent analyte models in surface plasmon resonance (SPR) sensorgrams, the method comprising:
  recording multiple SPR sensorgrams (i.e., a first batch, preferably comprising three or more recordings) with an analyte, with the analyte having a different concentration for each sensorgram (recording of a sensorgram can include measuring the analyte concentration);
  fitting each sensorgram with a single exponential function with exponents;
  determining the exponents for each sensorgram and $R^2$ values for each sensorgram; and
  plotting $R^2$ versus analyte concentration and determining if a maximum exists (i.e., determining if an optimal concentration exists).

Embodiment 2

The method of Embodiment 1, wherein the multiple surface plasmon resonance sensorgrams are conducted using equivalent sensor surfaces.

Embodiment 3

The method of any of Embodiments 1 to 2, wherein the single exponential function with exponents is $$Y(t) = \frac{B_0}{2}(1 - e^{-(2k_{a1}C_0 + k_{d1})t}) = \frac{B_0}{2}(1 - e^{-(4k_{a1}C_0)t}),$$

or an equivalent function.

Embodiment 4

The method of any of Embodiments 1 to 3, further comprising determining if the maximum $R^2$ value is over a threshold.

Embodiment 5

The method of any of Embodiments 1 to 4, further comprising determining if the plot of $R^2$ versus analyte concentration takes the form of a quadratic function.

Embodiment 6

The method of any of Embodiments 1 to 5, further comprising:
  fitting each sensorgram with a double exponential function, $R = D + Ee^{-\sigma_1 t} + Fe^{-\sigma_2 t}$ (association), $R = Ee^{-\gamma_1 t} + Fe^{-\gamma_2 t}$ (dissociation), or an equivalent exponential function, with D, E, F, σ1, σ2, γ1, and γ2 being fitting parameters and with D=−(E+F); and plotting σ1+σ2 versus analyte concentration and determining if the plot of σ1+σ2 versus analyte concentration is non-linear.

Embodiment 7

The method of Embodiment 6, wherein if the plot of σ1+σ2 versus analyte concentration is non-linear, it is concluded that a bivalent analyte reaction mechanism is present.

Embodiment 8

The method of any of Embodiments 6 to 7, wherein if the plot of σ1+σ2 versus analyte concentration is non-linear, it is concluded that a bivalent analyte reaction model is appropriate.

Embodiment 9

The method of any of Embodiments 1 to 8, wherein if a maximum exists that is greater than the $R^2$ threshold in the plot of $R^2$ versus analyte concentration, it is concluded that a bivalent analyte reaction mechanism is present.

Embodiment 10

The method of any of Embodiments 1 to 9, wherein if a maximum exists that is greater than the $R^2$ threshold in the plot of $R^2$ versus analyte concentration, it is concluded that a bivalent analyte reaction model is present.

Embodiment 11

The method of any of Embodiments 6 to 10, further comprising:
plotting $\sigma_1 * \sigma_2$ versus analyte concentration; and
determining if the plot of $\sigma_1 * \sigma_2$ versus analyte concentration is either linear or quadratic.

Embodiment 12

The method of Embodiment 11, wherein if the plot of $\sigma_1 * \sigma_2$ versus analyte concentration is either linear or quadratic, it is concluded that a bivalent analyte reaction mechanism is not present.

Embodiment 13

The method of any of Embodiments 11 to 12, wherein if the plot of $\sigma_1 * \sigma_2$ versus analyte concentration is either linear or quadratic, it is concluded that a bivalent analyte reaction model is not present.

Embodiment 14

The method of any of Embodiments 1 to 13, wherein the method is used in the medical or pharmaceutical fields for drug development, drug analysis, protein interactions, biomolecular interactions, and/or DNA interactions.

Embodiment 15

The method of any of Embodiments 1 to 13, wherein the method is used in the food or beverage industry for product quality control, product development, GMO testing, pesticide testing, and/or herbicide testing.

Embodiment 16

The method of any of Embodiments 1 to 13, wherein the method is used in veterinary medicine to treat animals, diagnose diseases, and/or to analyze biomolecular interactions.

Embodiment 17

The method of any of Embodiments 1 to 16, wherein the method is partially or completely implemented using a computing device, having one or more processors and memory, to increase measurement predictions and/or increase the efficiency of computing resources.

Embodiment 18

The method of any of Embodiments 1 to 17, wherein after the first batch of multiple SPR sensorgrams are recorded, a second batch of multiple SPR sensorgrams are recorded and the method steps of one or more of Embodiments 1 through 13 are conducted again to perfect the analysis (e.g., to better determine the "optimal concentration", better identify whether a bivalent analyte mechanism is present, and/or better understand the applicability of a bivalent analyte model).

Embodiment 19

The method of Embodiment 18, wherein after the second batch of multiple SPR sensorgrams are recorded, a third batch of multiple SPR sensorgrams are recorded and the method steps of one or more of Embodiments 1 through 13 are conducted again to perfect the analysis.

Embodiment 19

The method of any of Embodiments 1 to 18, further comprising preparing the analyte for sensorgram recording prior to recording the sensorgram(s) (which can be performed once or before each sensorgram recording).

Embodiment 101

A surface plasmon resonance (SPR) system comprising:
a machine for recording multiple SPR sensorgrams with an analyte, with the analyte having a different concentration for each sensorgram;
a (non-transitory) computer-readable (or machine-readable) medium with computer executable instructions stored thereon that when executed by a processor perform a method for identifying a bivalent reaction mechanism or bivalent analyte model, the method comprising:
inputting recordings of the multiple SPR sensorgrams (i.e., a first batch) with the analyte, with the analyte having a different concentration for each sensorgram;
fitting each sensorgram with a single exponential function with exponents;
determining the exponents for each sensorgram and $R^2$ values for each sensorgram; and
plotting $R^2$ versus analyte concentration and determining if a maximum exists (i.e., determining if an optimal concentration exists).

Embodiment 102

The system of Embodiment 101, wherein the multiple SPR sensorgrams are conducted using equivalent sensor surfaces.

Embodiment 103

The system of any of Embodiments 101 to 102, wherein the single exponential function with exponents is $$Y(t) = \frac{B_0}{2}(1 - e^{-(2k_{a1}C_0 + k_{d1})t}) = \frac{B_0}{2}(1 - e^{-(4k_{a1}C_0)t}).,$$

or an equivalent function.

Embodiment 104

The system of any of Embodiments 101 to 103, wherein the method further comprises determining if the maximum $R^2$ value is over a threshold.

Embodiment 105

The system of any of Embodiments 101 to 104, wherein the method further comprises determining if the plot of $R^2$ versus analyte concentration takes the form of a quadratic function.

Embodiment 106

The system of any of Embodiments 101 to 105, wherein the method further comprises:
fitting each sensorgram with a double exponential function, $R=D+Ee^{-\sigma_1 t}+Fe^{-\sigma_2 t}$ (association), $R=Ee^{-\gamma_1 t}+Fe^{-\gamma_2 t}$ (dissociation), or an equivalent exponential function, with D, E, F, $\sigma_1$, $\sigma_2$, $\gamma_1$, and $\gamma_2$ being fitting parameters and with D=−(E+F); and
plotting $\sigma_1+\sigma_2$ versus analyte concentration and determining if the plot of $\sigma_1+\sigma_2$ versus analyte concentration is non-linear.

Embodiment 107

The system of Embodiment 106, wherein if the plot of $\sigma_1+\sigma_2$ versus analyte concentration is non-linear, it is concluded that a bivalent analyte reaction mechanism is present.

Embodiment 108

The system of any of Embodiments 106 to 107, wherein if the plot of $\sigma_1+\sigma_2$ versus analyte concentration is non-linear, it is concluded that a bivalent analyte reaction model is appropriate.

Embodiment 109

The system of any of Embodiments 101 to 108, wherein if a maximum exists that is greater than the $R^2$ threshold in the plot of $R^2$ versus analyte concentration, it is concluded that a bivalent analyte reaction mechanism is present.

Embodiment 110

The system of any of Embodiments 101 to 109, wherein if a maximum exists in the plot of $R^2$ versus analyte concentration that is greater than the $R^2$ threshold, it is concluded that a bivalent analyte reaction model is appropriate.

Embodiment 111

The system of any of Embodiments 106 to 110, wherein the method further comprises:
plotting $\sigma_1*\sigma_2$ versus analyte concentration; and
determining if the plot of $\sigma_1*\sigma_2$ versus analyte concentration is either linear or quadratic.

Embodiment 112

The system of Embodiment 111, wherein if the plot of $\sigma_1*\sigma_2$ versus analyte concentration is either linear or quadratic, it is concluded that a bivalent analyte reaction mechanism is not present.

Embodiment 113

The system of any of Embodiments 111 to 112, wherein if the plot of $\sigma_1*\sigma_2$ versus analyte concentration is either linear or quadratic, it is concluded that a bivalent analyte reaction model is not appropriate.

Embodiment 114

The system of any of Embodiments 101 to 113, wherein the system is used in the medical or pharmaceutical fields for drug development, drug analysis, protein interactions, biomolecular interactions, and/or DNA interactions.

Embodiment 115

The system of any of Embodiments 101 to 113, wherein the system is used in the food or beverage industry for product quality control, product development, GMO testing, pesticide testing, and/or herbicide testing.

Embodiment 116

The system of any of Embodiments 101 to 113, wherein the system is used in veterinary medicine to treat animals, diagnose diseases, and/or analyze biomolecular interactions.

Embodiment 117

The system of any of Embodiments 101 to 116, wherein after the first batch of multiple SPR sensorgrams are recorded, a second batch of multiple SPR sensorgrams are recorded and the method steps of one or more of Embodiments 101 through 113 are conducted to perfect the analysis (e.g., to better determine the "optimal concentration", better identify whether a bivalent analyte mechanism is present, or better understand the applicability of a bivalent analyte model).

Embodiment 118

The system of Embodiment 117, wherein after the second batch of multiple SPR sensorgrams are recorded, a third batch of multiple SPR sensorgrams are recorded and the method steps of one or more of Embodiments 101 through 113 are conducted again to perfect the analysis.

Embodiment 201

A (non-transitory) computer-readable (or machine-readable) medium with computer executable instructions stored thereon that when executed by a processor perform a method for identifying a bivalent reaction mechanism or bivalent analyte model in surface plasmon resonance (SPR) sensorgrams, the method comprising:
  inputting recordings of multiple SPR sensorgrams (i.e., a first batch) with an analyte, with the analyte having a different concentration for each sensorgram;
  fitting each sensorgram with a single exponential function with exponents;
  determining the exponents for each sensorgram and $R^2$ values for each sensorgram; and
  plotting $R^2$ versus analyte concentration and determining if a maximum exists (i.e., determining if an optimal concentration exists).

Embodiment 202

The computer-readable (or machine-readable) medium of Embodiment 201, wherein the multiple SPR sensorgrams were conducted using equivalent sensor surfaces.

Embodiment 203

The computer-readable (or machine-readable) medium of any of Embodiments 201 to 202, wherein the single exponential function with exponents is $$Y(t) = \frac{B_0}{2}(1 - e^{-(2k_{a1}C_0 + k_{d1})t}) = \frac{B_0}{2}(1 - e^{-(4k_{a1}C_0)t}),$$

or an equivalent function.

Embodiment 204

The computer-readable (or machine-readable) medium of any of Embodiments 201 to 203, wherein the method further comprises determining if the maximum $R^2$ value is over a threshold.

Embodiment 205

The computer-readable (or machine-readable) medium of any of Embodiments 201 to 204, wherein the method further comprises determining if the plot of $R^2$ versus analyte concentration takes the form of a quadratic function.

Embodiment 206

The computer-readable (or machine-readable) medium of any of Embodiments 201 to 205, wherein the method further comprises:
  fitting each sensorgram with a double exponential function, $R = D + Ee^{-\sigma_1 t} + Fe^{-\sigma_2 t}$ (association), $R = Ee^{-\gamma_1 t} + Fe^{-\gamma_2 t}$ (dissociation), or an equivalent exponential function, with D, E, F, $\sigma_1$, $\sigma_2$, $\gamma_1$, and $\gamma_2$ being fitting parameters and with $D=-(E+F)$; and
  plotting $\sigma_1 + \sigma_2$ versus analyte concentration and determining if the plot of $\sigma_1 + \sigma_2$ versus analyte concentration is non-linear.

Embodiment 207

The computer-readable (or machine-readable) medium of Embodiment 206, wherein if the plot of $\sigma_1 + \sigma_2$ versus analyte concentration is non-linear, it is concluded that a bivalent analyte reaction mechanism is present.

Embodiment 208

The computer-readable (or machine-readable) medium of any of Embodiments 206 to 207, wherein if the plot of $\sigma_1 + \sigma_2$ versus analyte concentration is non-linear, it is concluded that a bivalent analyte reaction model is appropriate.

Embodiment 209

The computer-readable (or machine-readable) medium of any of Embodiments 201 to 208, wherein if a maximum exists that is greater than the $R^2$ threshold in the plot of $R^2$ versus analyte concentration, it is concluded that a bivalent analyte reaction mechanism is present.

Embodiment 210

The computer-readable (or machine-readable) medium of any of Embodiments 201 to 209, wherein if a maximum exists that is greater than the $R^2$ threshold in the plot of $R^2$ versus analyte concentration, it is concluded that a bivalent analyte reaction model is appropriate.

Embodiment 211

The computer-readable (or machine-readable) medium of any of Embodiments 206 to 210, wherein the method further comprises:
  plotting $\sigma_1 * \sigma_2$ versus analyte concentration; and
  determining if the plot of $\sigma_1 * \sigma_2$ versus analyte concentration is either linear or quadratic.

Embodiment 212

The computer-readable (or machine-readable) medium of Embodiment 211, wherein if the plot of $\sigma_1 * \sigma_2$ versus analyte concentration is either linear or quadratic, it is concluded that a bivalent analyte reaction mechanism is not present.

Embodiment 213

The computer-readable (or machine-readable) medium of any of Embodiments 211 to 212, wherein if the plot of $\sigma_1 * \sigma_2$ versus analyte concentration is either linear or quadratic, it is concluded that a bivalent analyte reaction model is not appropriate.

Embodiment 214

The computer-readable (or machine-readable) medium of any of Embodiments 201 to 213, wherein the method is used in the medical or pharmaceutical fields for drug development, drug analysis, protein interactions, biomolecular interactions, and/or DNA interactions.

Embodiment 215

The computer-readable (or machine-readable) medium of any of Embodiments 201 to 213, wherein the method is used in the food or beverage industry for product quality control, product development, GMO testing, pesticide testing, and/or herbicide testing.

Embodiment 216

The computer-readable (or machine-readable) medium of any of Embodiments 201 to 213, wherein the method is used in veterinary medicine to treat animals, diagnose diseases, and/or analyze biomolecular interactions.

Embodiment 217

The computer-readable (or machine-readable) medium of any of Embodiments 201 to 216, wherein the method increases measurement predictions or increases the efficiency of computing resources.

Embodiment 218

The computer-readable (or machine-readable) medium of any of Embodiments 201 to 217, wherein after the first batch of multiple surface plasmon resonance sensorgrams are inputted, a second batch of multiple surface plasmon resonance sensorgrams are inputted and the method steps of one or more of Embodiments 201 through 213 are conducted to perfect the analysis (to better determine the "optimal concentration", better identify whether a bivalent analyte mechanism is present, or better understand the applicability of a bivalent analyte model).

Embodiment 219

The computer-readable (or machine-readable) medium of Embodiment 218, wherein after the second batch of multiple SPR sensorgrams are recorded, a third batch of multiple SPR sensorgrams are recorded and the method steps of one or more of Embodiments 201 through 213 are conducted again to perfect the analysis.

Embodiment 301

The method of any of Embodiments 4 to 19, the system of any of Embodiments 104 to 118, or the computer-readable (or machine-readable) medium of any of Embodiments 204 to 219, wherein the threshold is 0.900.

Embodiment 302

The method of any of Embodiments 4 to 19, the system of any of Embodiments 104 to 118, or the computer-readable (or machine-readable) medium of any of Embodiments 204 to 219, wherein the threshold is 0.910.

Embodiment 303

The method of any of Embodiments 4 to 19, the system of any of Embodiments 104 to 118, or the computer-readable (or machine-readable) medium of any of Embodiments 204 to 219, wherein the threshold is 0.920.

Embodiment 304

The method of any of Embodiments 4 to 19, the system of any of Embodiments 104 to 118, or the computer-readable (or machine-readable) medium of any of Embodiments 204 to 219, wherein the threshold is 0.930.

Embodiment 305

The method of any of Embodiments 4 to 19, the system of any of Embodiments 104 to 118, or the computer-readable (or machine-readable) medium of any of Embodiments 204 to 219, wherein the threshold is 0.940.

Embodiment 306

The method of any of Embodiments 4 to 19, the system of any of Embodiments 104 to 118, or the computer-readable (or machine-readable) medium of any of Embodiments 204 to 219, wherein the threshold is 0.950.

Embodiment 307

The method of any of Embodiments 4 to 19, the system of any of Embodiments 104 to 118, or the computer-readable (or machine-readable) medium of any of Embodiments 204 to 219, wherein the threshold is 0.960.

Embodiment 308

The method of any of Embodiments 4 to 19, the system of any of Embodiments 104 to 118, or the computer-readable (or machine-readable) medium of any of Embodiments 204 to 219, wherein the threshold is 0.970.

Embodiment 309

The method of any of Embodiments 4 to 19, the system of any of Embodiments 104 to 118, or the computer-readable (or machine-readable) medium of any of Embodiments 204 to 219, wherein the threshold is 0.975.

Embodiment 310

The method of any of Embodiments 4 to 19, the system of any of Embodiments 104 to 118, or the computer-readable (or machine-readable) medium of any of Embodiments 204 to 219, wherein the threshold is 0.980.

Embodiment 311

The method of any of Embodiments 4 to 19, the system of any of Embodiments 104 to 118, or the computer-readable (or machine-readable) medium of any of Embodiments 204 to 219, wherein the threshold is 0.985.

Embodiment 312

The method of any of Embodiments 4 to 19, the system of any of Embodiments 104 to 118, or the computer-readable (or machine-readable) medium of any of Embodiments 204 to 219, wherein the threshold is 0.990.

Embodiment 313

The method of any of Embodiments 4 to 19, the system of any of Embodiments 104 to 118, or the computer-readable (or machine-readable) medium of any of Embodiments 204 to 219, wherein the threshold is 0.995.

Embodiment 314

The method of any of Embodiments 4 to 19, the system of any of Embodiments 104 to 118, or the computer-readable (or machine-readable) medium of any of Embodiments 204 to 219, wherein the threshold is 0.998.

Embodiment 315

The method of any of Embodiments 4 to 19, the system of any of Embodiments 104 to 118, or the computer-readable (or machine-readable) medium of any of Embodiments 204 to 219, wherein the threshold is 0.999.

A greater understanding of the present invention and of its many advantages may be had from the following example, given by way of illustration. The following example is illustrative of some of the methods, applications, embodiments and variants of the present invention. It is, of course, not to be considered as limiting the invention. Numerous changes and modifications can be made with respect to the invention.

Example 1

Figure 2:
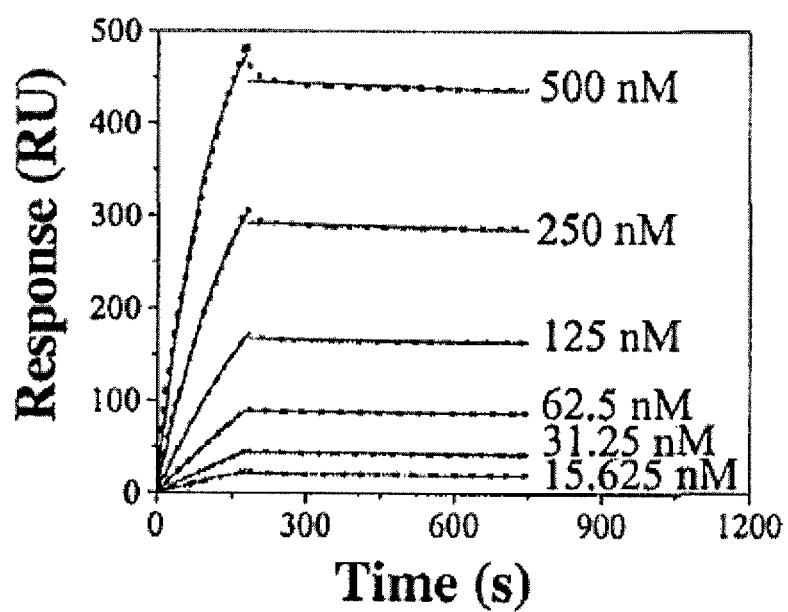
FIG. 2 shows a graph of SPR sensorgrams for ezrinAb binding to immobilized ezrin at different concentrations.

The approaches to identifying interactions that fit a bivalent analyte model and the occurrence of a bivalent reaction mechanism discussed in this application were tested in proof of concept experiments, which included experimentally measured SPR sensorgrams. A BIACORE T200 instrument was used to record SPR sensorgrams. Sensor chip CM5 was used to immobilize recombinant ezrin proteins onto the sensor surface via standard amine coupling chemistry. Various concentrations (15.625 nM-500 nM) of anti-ezrin monoclonal antibody (ezrinAb) were passed through the ezrin immobilized sensor surface. FIG. 2 depicts the SPR sensorgrams for ezrinAb-ezrin binding. As shown in FIG. 2, the SPR association profiles did not reach an equilibrium state and, as a result, the simplest equilibrium data analysis method cannot be used. The lowest $R^2$ value of fitting of both association and dissociation profiles (FIG. 2) was less than 0.75. This indicates that the interaction mechanism was not 1:1. The SPR sensorgrams were therefore fitted using the following double exponential functions:

$$R=D+Ee^{-\sigma_1 t}+Fe^{-\sigma_2 t} \text{ (association)},$$

$$R=Ee^{-\gamma_1 t}+Fe^{-\gamma_2 t} \text{ (dissociation)},$$

where D, E, F, $\sigma_1$, $\sigma_2$, $\gamma_1$, and $\gamma_2$ are fitting parameters with $D=-(E+F)$. The lowest $R^2$ value of the fitting of the SPR sensorgram was better than 0.97 (data not shown).

Table 1, below, gives on an analysis on how to use the fitting parameters derived from Equations (7) and (8) to determine appropriate mechanism or model. There are three commonly used models for the linear biphasic reaction, they are: Model 1 (the heterogeneous ligand model); Model 2 (the two-step conformational change model), and Model 3 (the bivalent ligand model). Of course, the focus of the application is Model 4 (the bivalent analyte model).

TABLE 1

| | Fitting parameters | | |
|---|---|---|---|
| Model | $\sigma_1\sigma_2$ vs C | $\sigma_1$ and $\sigma_2$ vs C | $\sigma_1 + \sigma_2$ vs C |
| 1 | Non-linear | Linear | Linear |
| 2 | Linear | Non-linear | Linear |
| 3 | Non-linear | Non-linear | Linear |
| 4 | Non-linear | Non-linear | Non-linear |

As discussed in the related art, a "good" global fitting quality cannot guarantee the correct identification of the underlying mechanism. The behavior of the exponents (fitting parameters, Equation (7)) as a function of the analyte concentration should also be examined. The dependency of the sum of the exponents on ezrinAb concentration as shown in FIG. 3(a) shows that the underlying mechanism is none of the three models discussed in detail in Tiwari et al. (Rev. Sci. Jnstrnm. 86, 035001 (2015); reference 13 in the "References" section below), which is hereby incorporated herein by reference in its entirety. In addition, the product of the exponents should be either linear (two-step conformational change model) or quadratic (heterogeneous ligand model and bivalent ligand model) for the biphasic mechanism to be any of the three biphasic mechanisms. As shown in Tiwari et al., the quadratic dependency must have positive coefficients (coefficients of the quadratic, linear, and constant term in a quadratic equation). The dependency of the product of the exponents as shown in FIG. 3(b) therefore added another validation that the underlying mechanism is not any of the biphasic mechanisms as explained above. Notably, the biphasic models (two-step conformational change model, heterogeneous ligand model, and bivalent ligand model) are governed by coupled system of linear differential equations, unlike the bivalent analyte model presented in this report.

Finally, to correctly identify the underlying biphasic model, the signature of the bivalent analyte model explained above was utilized. The distribution of the $R^2$ value obtained by fitting SPR association profiles at different analyte concentrations with a single exponential function (FIG. 2) is shown in FIG. 4.

The distribution of $R^2$ values for the experimental data followed the theoretical model as predicted by Equations (4) and (6). Therefore, the underlying biphasic mechanism for ezrinAb-ezrin binding should be the bivalent analyte. The monoclonal anti-ezrin antibody is an $I_gG_1$ type antibody, which has two Fab portions for binding to ezrin. Therefore, the $I_gG$ antibody represents a good model for a bivalent analyte. From the fitting of the SPR association profiles (FIG. 2), the "optimal concentration" is determined to be 62.5 nM. Once the "optimal concentration" is determined, Equation (6) can be used to determine the $k_{a1}$ and $k_{d1}$ and hence the equilibrium dissociation constant ($K_{D1}$) of the interaction ($K_{D1}=k_{d1}/k_{a1}$) corresponding to the first phase of the interaction. The $k_{a1}$, $k_{d1}$, and $K_{D1}$ values were determined to be $0.74\times10^4$ $M^{-1}$ $s^{-1}$, $0.92\times10^{-3}$ $s^{-1}$, and ~124 nM, respectively.

Experimental SPR sensorgrams were measured by using BIACORE T200 instrument available in the BIACORE Molecular Interaction Shared Resource (BMISR) facility at Georgetown University. The BMISR is supported by National Institutes of Health Grant No. P30CA51008.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. E. M. Phizicky and S. Fields, Microbiol. Rev. 59, 94 (1995).
2. P. B. Tiwari, L. Astudillo, J. Miksovska, X. Wang, W. Li, Y. Darici, and J. He, Nanoscale 6, 10255 (2014).
3. T. Berggard, S. Linse, and P. James, Proteomics 7, 2833 (2007).
4. J. Majka and C. Speck, in Analytics of Protein-DNA Interactions, edited by H. Seitz (Springer, Berlin Heidelberg, 2007).

5. P. Y. Tsoi and M. Yang, Biosens. Bioelecrron. 19, 1209 (2004).
6. P. B. Tiwari, T. Annamalai, B. Cheng, G. Narula, X. Wang, Y.-C. Tse-Dinh, J. He, and Y. Darici, Biochem. Biophys. Res. Commun. 445, 445 (2014).
7. W. Wang, Y. Yang, S. Wang, V. J. Nagaraj, Q. Liu, J. Wu, and N. Tao, Nat. Chem. 4, 846 (2012).
8. A. T6th, E. Kiss, F. W. Herberg, P. Gergely, D. J. Hartshorne, and F. ErdOdi, Eur. J. Biochem. 267, 1687 (2000).
9. S. Filion-Cote, P. J. R. Roche, A. M. Foudeh, M. Tabrizian, and A. G. Kirk, Rev. Sci. Instrum. 85, 093107 (2014).
10. H. Q. Zhang, S. Boussaad, and N. J. Tao, Rev. Sci. Instrum. 74, 150 (2003).
11. N. J. Tao, S. Boussaad, W. L. Huang, R. A. Arechabaleta, and J. D'Agnese, Rev. Sci. Instrum. 70, 4656 (1999).
12. O. G. Myszka and T. A. Morton, Trends Biochem. Sci. 23, 149 (1998).
13. P. B. Tiwari, X. Wang, J. He, and Y. Darici, Rev. Sci. Instrum. 86, 035001 (2015).
14. K. J. James, M. A. Hancock, V. Moreau, F. Molina, anc! J. W. Coulton, Protein Sci. 17, 1679 (2008).
15. S. M. Solbak, V. Wray, O. Horvli, A. J. Raae, M. I. Flyda, P. Henklein, P.
16. Henklein, M. Nimtz, U. Schubert, and T. Fossen, BMC Struct. Biol. 11, 49 (2011).
17. H. Nakajima, N. Kiyokawa, Y. U. Katagiri, T. Taguchi, T. Suzuki, T. Sekino, K. Mimori, T. Ebata, M. Saito, H. Nakao, T. Takeda, and J. Fujimoto, J. Biol. Chem. 276, 42915 (2001).
18. K. B. Pabbisetty, X. Yue, C. Li, J.-P. Himanen, R. Zhou, D. B. Nikolov, and L. Hu, Protein Sd. 16, 355 (2007).
19. Gutierrez-Aguirre, V. Hodnik, L. Glais, M. Rupar, E. Jacquot, G. Ander-luh, and M. Ravnikar, Anal. Biochem. 447, 74 (2014).
A. K. A. Smith, P. J. Adamson, R. J. Pease, J. M. Brown, A. J. Balmforth, P, Cordell, R. A. S. Ariens, H. Philippou, and P. J. Grant, Blood 117, 3460 (2011).
20. B. Murthy and N. Jayaraman, J. Chem. Sd. 120, 195 (2008).
21. T. Suzuki, A. Ishii-Watabe, M. Tada, T. Kobayashi, T. Kanayasu-Toyoda, T. Kawanishi, and T. Yamaguchi, J. Inummol. 184, 1968 (2010).
22. S. N. Prince, E. J. Foulstone, O. J. Zaccheo, C. Williams, and A. B. Hassan, Mol. Cancer Ther. 6, 607 (2007).
23. K. Haupt, M. Reuter, J. van den Elsen, J. Burman, S. Hlilbich, J. Richter, C. Skerka, and P. F. Zipfel, PLoS Pathog. 4, e1000250 (2008).
24. W. D. Wilson, Science 295, 2103 (2002).
25. D. G. Myszka, Curr. Opin. Biotechnol. 8, 50 (1997).
26. B. Nguyen, F. A. Tanious, and W. D. Wilson, Methods 42, 150 (2007).
27. S. C. Schuster, R. V. Swanson, L. A. Alex, R. B. Bourret, and M. I. Simon, Nature 365, 343 (1993).
28. N.-F. Chiu and T.-Y. Huang, Sens. Actuators, B 197, 35 (2014).
29. B. Sikarwar, P. K. Sharma, A. Srivastava, G. S. Agarwal, M. Boopathi, B. Singh, and Y. K. Jaiswal, Biosens. Bioelectron. 60, 201 (2014).
30. R. K. Somvanshi, A. Kumar, S. Kant, D. Gupta, S. B. Singh, U. Das, A. Srinivasan, T. P. Singh, and S. Dey, Biochem. Biophys. Res. Commun. 361, 37 (2007).
31. N. M. Mulchan, M. Rodriguez, K. O'Shea, and Y. Darici, Sens. Actuators, B 88, 132 (2003).
32. P. Critchley, J. Kazlauskaite, R. Eason, and T. J. T. Pinheiro, Biochem. Biophys. Res. Commun. 313, 559 (2004).
33. P. A. Van der Merwe, *Protein-Ligand Interactions: Hydrodynamics Calorimetry*, edited by S. Harding and B. Z. Chowdhry (Oxford University Press, Oxford, U K, 2001).
34. C. Hahnefeld, S. Drewianka, and F. Herberg, in *Molecular Diagnosis of Infectious Diseases*, edited by J. Decler and U. Reischl (Humana Press, New Jersey, 2004).
35. S. Filion-Cote, P. J. R. Roche, A. M. Foudeh, M. Tabrizian, and A. G. Kirk, Rev. Sci. Instrum. 85, 093107 (2014).
36. S. Lund-Katz, D. Nguyen, P. Dhanasekaran, M. Kono, M. Nickel, H. Saito, and M. C. Phillips, J. Lipid Res. 51, 606 (2010).
37. D. Riesner, A. Pingoud, D. Boehme, F. Peters, and G. Maass, Eur. J. Biochem. 68, 71 (1976).
38. J. Bernet, J. Mullick, Y. Panse, P. B. Parah, and A. Sahu, J. Virol. 78, 9446 (2004).
39. W. L. Martin and P. J. Bjorkman, Biochemistry 38, 12639 (1999).
40. R. L. Rich and D. G. Myszka, J. Mol. Recognit. 19, 478 (2006).
41. F. Gesellchen, B. Zimmermann, and F. Herberg, *Protein-Ligand Interactions*, edited by G. U. Nienhaus (Humana Press, New Jersey, 2005).
42. M. Ghiotto, L. Gauthier, N. Serriari, S. Pastor, A. Truneh, J. A. Nunes, and D. Olive, Int. Immunol. 22, 651 (2010).
43. D. Wawrzak, M. Metioui, E. Willems, M. Hendrickx, E. de Genst, and L. Leyns, Biochem. Biophys. Res. Commun. 357, 1119 (2007).
44. A. Datta-Mannan, C.-K. Chow, C. Dickinson, C. Driver, J. Lu, D. R. Witcher, and V. J. Wroblewski, Drug Metab. Dispos. 40, 1545 (2012).
45. N. J. de Mo!, M. I. Catalina, M. J. E. Fischer, I. Broutin, C. S. Maier, and A. J. R. Heck, Biochim. Biophys. Acta, Proteins Proteomics 1700, 53 (2004).
46. M. Futamura, P. Dhanasekaran, T. Handa, M. C. Phillips, S. Lund-Katz, and H. Saito, J. Biol. Chem. 280, 5414 (2005).
47. S. M. Alam, G. M. Davies, C. M. Lin, T. Zal, W. Nasholds, S. C. Jameson, K. A. Hogquist, N. R. J. Gascoigne, and P. J. Travers, Immunity 10, 227 (1999).
48. D. J. O'Shannessy and D. J. Winzor, Anal. Biochem. 236, 275 (1996).
49. E. R. Sprague, W. L. Martin, and P. J. Bjorkman, J. Biol. Chem. 279, 14184 (2004).
50. A. M. Giannetti, P. M. Snow, O. Zak, and P. J. Bjorkman, PLoS Biol. 1, e51 (2003).
51. Y.-S. Lo, W.-H. Tseng, C.-Y. Chuang, and M.-H. Hou, Nucleic Acids Res. 41, 4284 (2013).
52. M. L. Azoitei, Y.-E. A. Ban, J.-P. Julien, S. Bryson, A. Schroeter, O. Kalyuzhniy, J. R. Porter, Y. Adachi, D. Baker, E. F. Pai, and W. R. Schief, J. Mol. Biol. 415, 175 (2012).
53. T. A. Morton, D. G. Myszka, and I. M. Chaiken, Anal. Biochem. 227, 176 (1995).

What is claimed is:

1. A method for identifying a bivalent reaction mechanism or bivalent analyte models in surface plasmon resonance (SPR) sensorgrams, the method comprising:
   recording a first batch of multiple SPR sensorgrams with an analyte, with the analyte having a different concentration for each sensorgram;
   fitting each sensorgram with a single exponential function with exponents;

determining the exponents for each sensorgram and $R^2$ values for each sensorgram; and plotting $R^2$ versus analyte concentration and determining whether there is an optimal concentration, the single exponential function with exponents being $$Y(t) = \frac{B_0}{2}(1 - e^{-(2k_{a1}C_0 + k_{d1})t}) = \frac{B_0}{2}(1 - e^{-(4k_{a1}C_0)t}),$$

where $B_0$ is an initial ligand concentration, $k_{a1}$ is an association rate constant of a first ligand binding, $k_{d1}$ is a dissociation rate constant of the first ligand unbinding, $C_0$ is the optimal concentration and equals $-k_{d1}/2k_{a1}$, and t is time, and the method further comprising determining if the plot of $R^2$ versus analyte concentration takes the form of a quadratic function.

2. The method according to claim 1, further comprising determining if the optimal concentration $R^2$ value is over a threshold and, if a maximum exists that is greater than the $R^2$ threshold in the plot of $R^2$ versus analyte concentration, a bivalent analyte reaction mechanism is indicated or a bivalent analyte reaction model is applied.

3. The method according to claim 1, further comprising: fitting each sensorgram with a double exponential function, $R = D + Ee^{-\sigma_1 t} + Fe^{-\sigma_2 t}$ (association), $R = Ee^{-\gamma_1 t} + Fe^{-\gamma_2 t}$ (dissociation), wherein D, E, F, $\sigma_1$, $\sigma_2$, $\gamma_1$, and $\gamma_2$ are fitting parameters and $D = -(E+F)$; and plotting $\sigma_1 + \sigma_2$ versus analyte concentration and determining if the plot of $\sigma_1 + \sigma_2$ versus analyte concentration is non-linear.

4. The method according to claim 3, wherein if the plot of $\sigma_1 + \sigma_2$ versus analyte concentration is non-linear, a bivalent analyte reaction mechanism is indicated or a bivalent analyte reaction model is applied.

5. The method according to claim 3, further comprising: plotting $\sigma_1 * \sigma_2$ versus analyte concentration;

determining if the plot of $\sigma_1 * \sigma_2$ versus analyte concentration is either linear or quadratic; and if the plot of $\sigma_1 * \sigma_2$ versus analyte concentration is either linear or quadratic, a bivalent analyte reaction mechanism is not indicated or a bivalent analyte reaction model is not applied.

6. A method for identifying a bivalent reaction mechanism or bivalent analyte models in surface plasmon resonance (SPR) sensorgrams, the method comprising:

recording a first batch of multiple SPR sensorgrams with an analyte, with the analyte having a different concentration for each sensorgram;

fitting each sensorgram with a single exponential function with exponents;

determining the exponents for each sensorgram and $R^2$ values for each sensorgram; and plotting $R^2$ versus analyte concentration and determining whether there is an optimal concentration, the single exponential function with exponents being $$Y(t) = \frac{B_0}{2}(1 - e^{-(2k_{a1}C_0 + k_{d1})t}) = \frac{B_0}{2}(1 - e^{-(4k_{a1}C_0)t}),$$

where $B_0$ is an initial ligand concentration, $k_{a1}$ is an association rate constant of a first ligand binding, $k_{d1}$ is a dissociation rate constant of the first ligand unbinding, $C_0$ is the optimal concentration and equals $-k_{d1}/2k_{a1}$, and t is time, the method further comprising:

determining if the optimal concentration $R^2$ value is over a threshold and, if a maximum exists that is greater than the $R^2$ threshold in the plot of $R^2$ versus analyte concentration, a bivalent analyte reaction mechanism is indicated or a bivalent analyte reaction model is applied;

if the optimal concentration $R^2$ value is not over the threshold, recording a second batch of multiple SPR sensorgrams with an analyte, with the analyte having a different concentration for each sensorgram, and the concentrations being focused around a predicted optimum concentration determined from the first batch;

fitting each sensorgram of the second batch with a single exponential function with exponents;

determining the exponents for each sensorgram of the second batch and $R^2$ values for each sensorgram of the second batch; and plotting $R^2$ versus analyte concentration of the second batch and determining whether there is an optimal concentration.

7. A non-transitory machine-readable medium with computer executable instructions stored thereon that when executed by a processor perform a method for identifying a bivalent reaction mechanism or bivalent analyte model in surface plasmon resonance (SPR) sensorgrams, the method comprising:

inputting recordings of a first batch of multiple SPR sensorgrams with an analyte, with the analyte having a different concentration for each sensorgram;

fitting each sensorgram with a single exponential function with exponents;

determining the exponents for each sensorgram and $R^2$ values for each sensorgram; and plotting $R^2$ versus analyte concentration and determining whether there is an optimal concentration, the single exponential function with exponents being $$Y(t) = \frac{B_0}{2}(1 - e^{-(2k_{a1}C_0 + k_{d1})t}) = \frac{B_0}{2}(1 - e^{-(4k_{a1}C_0)t}),$$

where $B_0$ is an initial ligand concentration, $k_{a1}$ is an association rate constant of a first ligand binding, $k_{d1}$ is a dissociation rate constant of the first ligand unbinding, $C_0$ is the optimal concentration and equals $-k_{d1}/2k_{a1}$, and t is time, and the method further comprising determining if the plot of $R^2$ versus analyte concentration takes the form of a quadratic function.

8. The machine-readable medium according to claim 7, wherein the method further comprises determining if the optimal concentration $R^2$ value is over a threshold and, if a maximum exists that is greater than the $R^2$ threshold in the plot of $R^2$ versus analyte concentration, a bivalent analyte reaction mechanism is indicated or a bivalent analyte reaction model is applied.

9. The machine-readable medium according to claim 7, wherein the method further comprises:
  fitting each sensorgram with a double exponential function,
  $$R=D+Ee^{-\sigma_1 t}+Fe^{-\sigma_2 t} \text{ (association)},$$
  $$R=Ee^{-\gamma_1 t}+Fe^{-\gamma_2 t} \text{ (dissociation)},$$
  wherein D, E, F, $\sigma_1$, $\sigma_2$, $\gamma_1$, and $\gamma_2$ are fitting parameters and D=−(E+F); and
  plotting $\sigma_1+\sigma_2$ versus analyte concentration and determining if the plot of $\sigma_1+\sigma_2$ versus analyte concentration is non-linear.

10. The machine-readable medium according to claim 9, wherein if the plot of $\sigma_1+\sigma_2$ versus analyte concentration is non-linear, a bivalent analyte reaction mechanism is indicated or a bivalent analyte reaction model is applied.

11. The machine-readable medium according to claim 9, wherein the method further comprises:
  plotting $\sigma_1*\sigma_2$ versus analyte concentration;
  determining if the plot of $\sigma_1*\sigma_2$ versus analyte concentration is either linear or quadratic; and
  if the plot of $\sigma_1*\sigma_2$ versus analyte concentration is either linear or quadratic, a bivalent analyte reaction mechanism is not indicated or a bivalent analyte reaction model is not applied.

12. A non-transitory machine-readable medium with computer executable instructions stored thereon that when executed by a processor perform a method for identifying a bivalent reaction mechanism or bivalent analyte model in surface plasmon resonance (SPR) sensorgrams, the method comprising:
  inputting recordings of a first batch of multiple SPR sensorgrams with an analyte, with the analyte having a different concentration for each sensorgram;
  fitting each sensorgram with a single exponential function with exponents;
  determining the exponents for each sensorgram and $R^2$ values for each sensorgram; and
  plotting $R^2$ versus analyte concentration and determining whether there is an optimal concentration,
  the single exponential function with exponents being $$Y(t) = \frac{B_0}{2}(1 - e^{-(2k_{a1}C_0+k_{d1})t}) = \frac{B_0}{2}(1 - e^{-(4k_{a1}C_0)t}),$$

where $B_0$ is an initial ligand concentration, $k_{a1}$ is an association rate constant of a first ligand binding, $k_{d1}$ is a dissociation rate constant of the first ligand unbinding, $C_0$ is the optimal concentration and equals $-k_{d1}/2k_{a1}$, and t is time,
  the method further comprising determining if the optimal concentration $R^2$ value is over a threshold and, if a maximum exists that is greater than the $R^2$ threshold in the plot of $R^2$ versus analyte concentration, a bivalent analyte reaction mechanism is indicated or a bivalent analyte reaction model is applied, and
  the threshold being 0.980.

13. A non-transitory machine-readable medium with computer executable instructions stored thereon that when executed by a processor perform a method for identifying a bivalent reaction mechanism or bivalent analyte model in surface plasmon resonance (SPR) sensorgrams, the method comprising:
  inputting recordings of a first batch of multiple SPR sensorgrams with an analyte, with the analyte having a different concentration for each sensorgram;
  fitting each sensorgram with a single exponential function with exponents;
  determining the exponents for each sensorgram and $R^2$ values for each sensorgram; and
  plotting $R^2$ versus analyte concentration and determining whether there is an optimal concentration,
  the single exponential function with exponents being $$Y(t) = \frac{B_0}{2}(1 - e^{-(2k_{a1}C_0+k_{d1})t}) = \frac{B_0}{2}(1 - e^{-(4k_{a1}C_0)t}),$$

where $B_0$ is an initial ligand concentration, $k_{a1}$ is an association rate constant of a first ligand binding, $k_{d1}$ is a dissociation rate constant of the first ligand unbinding, $C_0$ is the optimal concentration and equals $-k_{d1}/2k_{a1}$, and t is time,
  the method further comprising:
  determining if the optimal concentration $R^2$ value is over a threshold and if a maximum exists that is greater than the $R^2$ threshold in the plot of $R^2$ versus analyte concentration, a bivalent analyte reaction mechanism is indicated or a bivalent analyte reaction model is applied;
  if the optimal concentration $R^2$ value is not over the threshold, recording a second batch of multiple SPR sensorgrams with an analyte, with the analyte having a different concentration for each sensorgram, and the concentrations being focused around a predicted optimum concentration determined from the first batch;
  fitting each sensorgram of the second batch with a single exponential function with exponents;
  determining the exponents for each sensorgram of the second batch and $R^2$ values for each sensorgram of the second batch; and
  plotting $R^2$ versus analyte concentration of the second batch and determining whether there is an optimal concentration.

* * * * *